(12) United States Patent
Liu et al.

(10) Patent No.: US 9,150,445 B2
(45) Date of Patent: Oct. 6, 2015

(54) POLYHYDROXYALKANOATE PRODUCTION DURING WASTEWATER TREATMENT

(76) Inventors: Hsin-Ying Liu, Sacramento, CA (US); Michael Wayne Falk, Jr., Sacramento, CA (US)

( * ) Notice: Subject to any disclaimer, the term of this patent is extended or adjusted under 35 U.S.C. 154(b) by 124 days.

(21) Appl. No.: 13/206,327

(22) Filed: Aug. 9, 2011

(65) Prior Publication Data

US 2013/0040351 A1  Feb. 14, 2013

(51) Int. Cl.
*C02F 3/12* (2006.01)
*C12P 7/62* (2006.01)
*C02F 3/34* (2006.01)

(52) U.S. Cl.
CPC ............ *C02F 3/1263* (2013.01); *C02F 3/1221* (2013.01); *C02F 3/34* (2013.01); *C12P 7/625* (2013.01); *C02F 2209/001* (2013.01); *C02F 2209/10* (2013.01); *Y02W 10/15* (2015.05); *Y02W 10/45* (2015.05)

(58) Field of Classification Search
None
See application file for complete search history.

(56) References Cited

U.S. PATENT DOCUMENTS

| | | | |
|---|---|---|---|
| 5,240,597 | A | 8/1993 | Ueda |
| 5,624,563 | A | 4/1997 | Hawkins |
| 6,737,263 | B2 | 5/2004 | Dragotta et al. |
| 6,987,011 | B1 | 1/2006 | Reid et al. |
| 6,991,931 | B2 | 1/2006 | Dragotta et al. |
| 7,267,974 | B2 | 9/2007 | Kozaki et al. |
| 7,435,566 | B2 | 10/2008 | Ogawa et al. |
| 7,514,525 | B2 | 4/2009 | Yu |
| 7,579,176 | B2 | 8/2009 | Herrema et al. |
| 7,887,893 | B2 | 2/2011 | Billington et al. |

(Continued)

FOREIGN PATENT DOCUMENTS

| | | |
|---|---|---|
| WO | 2011070544 A1 | 6/2011 |
| WO | 2011073744 A1 | 6/2011 |

OTHER PUBLICATIONS

Coats et al., Functional Stability of a Mixed Microbial Consortium Producing PHA From Waste Carbon Sources., Applied Biochemistry and Biotechnology (2007), vol. 136-140, pp. 909-925.*

(Continued)

*Primary Examiner* — Alexander Kim
(74) *Attorney, Agent, or Firm* — Shook, Hardy & Bacon L.L.P.

(57) ABSTRACT

A wastewater treatment process elicits microorganisms to convert a waste stream/organic resource to intracellular biopolymer polyhydroxyalkanoate (PHA). The process includes (i) waste stream/organic resource composition feed criteria, (ii) configuration coupled with operational parameters, and (iii) PHA-laden biomass separation and stabilization. A waste stream/organic resource capable of producing enhanced levels of PHA may be selected based on a combination of criteria, which may include short chain fatty acid concentration, protein concentration, polysaccharides concentration, and total suspended solids concentration. The waste stream is introduced into an aeration basin upon a specific configuration and operated under various parameter combinations for selecting/enriching microorganisms capable of producing PHA. The PHA-laden biomass is separated and stabilized for downstream PHA related product beneficial uses. The present process achieves concurrent wastewater treatment and PHA production, where PHA level (of more than 10% on a cell-weight basis) otherwise could not be obtained.

19 Claims, 2 Drawing Sheets

(56) References Cited

U.S. PATENT DOCUMENTS

| | | | |
|---|---|---|---|
| 2002/0031812 | A1 | 3/2002 | Lapointe et al. |
| 2002/0052016 | A1 | 5/2002 | Dragotta et al. |
| 2004/0152151 | A1* | 8/2004 | Dragotta et al. ............ 435/34 |
| 2007/0202581 | A1 | 8/2007 | Herrema et al. |
| 2008/0203015 | A1 | 8/2008 | Marston et al. |
| 2009/0317879 | A1 | 12/2009 | Criddle et al. |
| 2010/0035313 | A1 | 2/2010 | Satou et al. |
| 2010/0078389 | A1 | 4/2010 | Elektorowicz et al. |
| 2010/0190221 | A1 | 7/2010 | Herrema et al. |
| 2010/0200498 | A1 | 8/2010 | Bengtsson et al. |
| 2010/0255540 | A2 | 10/2010 | Herrema et al. |
| 2011/0104767 | A1 | 5/2011 | Kawata et al. |

OTHER PUBLICATIONS

Chiellini et al. (2001), Biorelated Polymers: Sustainable Polymer Science and Technilogy, L;iwer Academic/Plenum Publishers, New York, p. 134.*

Liu, Hsin-Ying, et al., Production of Polyhydroxyalkanoate During Treatment of Tomato Cannery Wastewater, Water Environment Research, vol. 80, No. 4, Apr. 2008.

Liu, Hsin-Ying, et al., Factorial Experimental Designs for Enhancement of Concurrent Ply(Hydroxyalkanoate) Production and Brewery Wastewater Treatment, Water Environment Research, vol. 83, No. 1, Jan. 2011.

Dionisi, Davide, et al., Biodegradable Polymers From Organic Acids by Using Activated Sludge Enriched by Aerobic Periodic Feeding, Biotochnology and Bioengineering, vol. 85, No. 6 Mar. 20, 2004.

Coats, Erik R., et al., Toward Polyhydroxyalkanoate Production Concurrent with Municipal Wastewater Treatment in a Sequencing Batch Reactor System, Journal of Environmental Engineering, pp. 46-54, Jan. 2011.

Takabatake, H., et al., Recovery of biodegradable plastics from activated sludge process, Water Science and Technology, vol. 42 Nos. 3-4 pp. 351-356, IWA Publishing 2000.

International Search Report and Written Opinion of PCT/US2012/049828, mailed Oct. 16, 2012.

Hsin-Ying. Bioplastics Poly(hydroxyalkanoate) Production During Industrial Wastewater Treatment. University of California—Davis. 2009. [retrieved on Sep. 21, 2012]. Retrieved from ProQuest/ <URL: http://search.proquest.com/docview/304858684/1395FBB21FA4A1D8C68/2?accountid=142944>. entire document.

* cited by examiner

POLYHYDROXYALKANOATE PRODUCTION DURING WASTEWATER TREATMENT

BACKGROUND

Polyhydroxyalkanoates (PHAs) are biologically derived polymers (or bioplastic) synthesized as intracellular storage materials by microorganisms metabolizing renewable organic carbon sources. The physical properties of PHA polymers are similar to those of conventional plastics (such as polypropylene (PP) and polyethylene (PE)). In contrast with traditional petroleum-based plastics, biomass-derived PHAs are generated from renewable carbon resources and are 100% biodegradable following disposal. Experts within the field consider PHAs as a potential "green" substitute to conventional plastics.

SUMMARY

Embodiments of the invention are defined by the claims below, not this summary. A high-level overview of various aspects of the invention are provided here for that reason, to provide an overview of the disclosure, and to introduce a selection of concepts that are further described in the detailed description section below. This summary is not intended to identify key features or essential features of the claimed subject matter, nor is it intended to be used as an aid in isolation to determine the scope of the claimed subject matter.

Embodiments of the present invention relate to enhanced polyhydroxyalkanoates (PHAs) production during wastewater treatment. A waste stream/organic resource that is suitable for increased PHA production may initially be identified based on a combination of constituents criteria. The criteria may include total suspended solids, short chain fatty acids concentration, protein concentration, and polysaccharides concentration. In some embodiments, the waste stream/organic resource may optionally be pre-treated to provide the constituents criteria. The waste stream/organic resource is introduced into an aeration basin that may be operated under conditions for selecting and enhancing microorganisms capable of accumulating PHA. PHA-laden biomass is separated and stabilized for beneficial PHA use.

BRIEF DESCRIPTION OF THE DRAWINGS

Embodiments of the present invention are described in detail below with reference to the attached drawing figures, and wherein.

DETAILED DESCRIPTION

Figure 1:
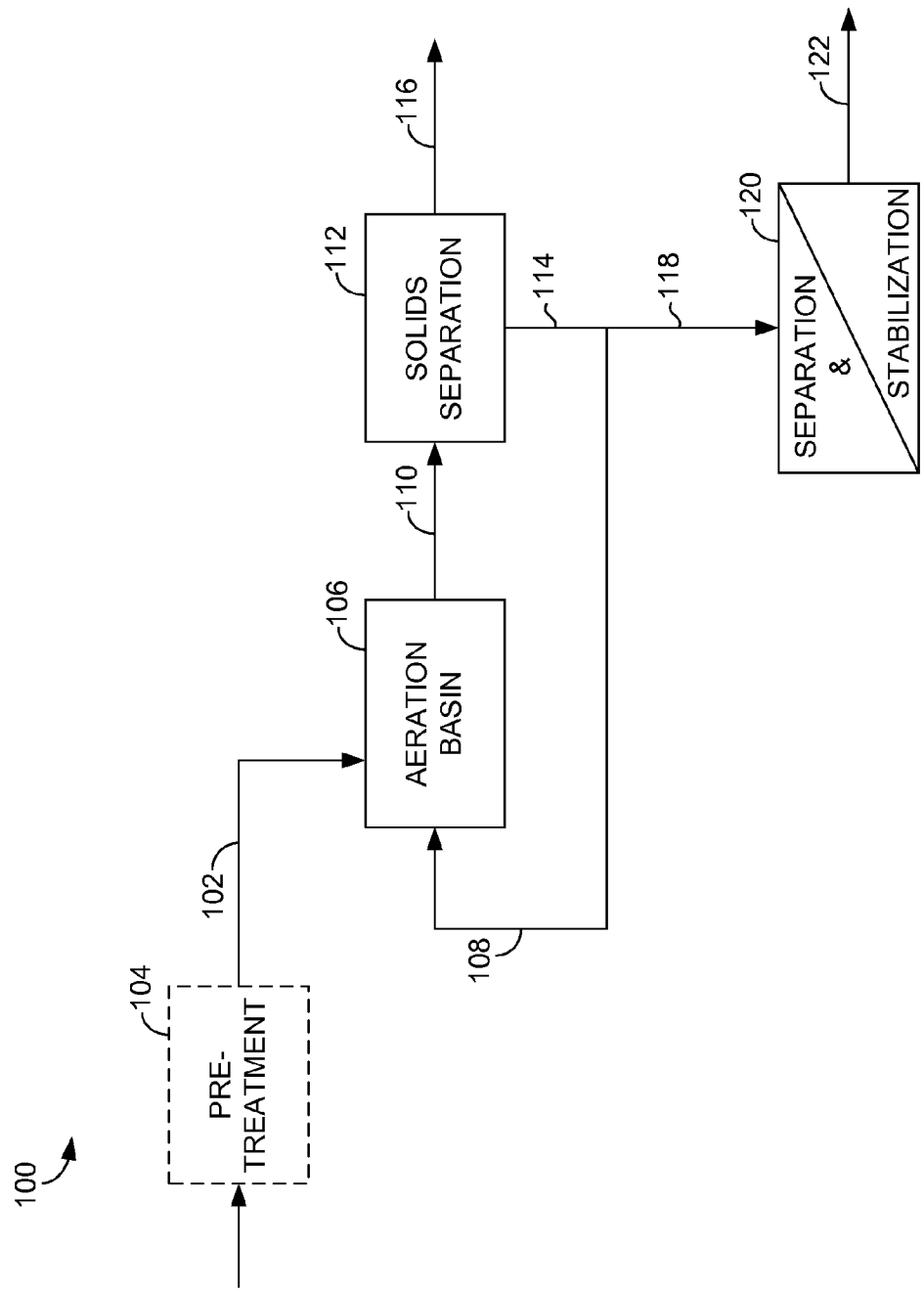
FIG. 1 illustrates a schematic diagram of PHA production during waste stream reclamation/organic resource recovery in accordance with an embodiment of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are generally directed to producing increased polyhydroxyalkanoates (PHAs) during treatment of wastewater by converting the organic matter in the wastewater into intracellular PHA during an activated sludge (AS) process. Accordingly, the process achieves simultaneous wastewater treatment performance and increased PHA production within a bioreactor. In conventional/regular wastewater treatment process, the PHA in AS is typically less than 2.5% on a cell-weight basis. In contrast, embodiments of the present invention may produce AS with PHA above 10% on a cell-weight basis.

While conventional AS processes are designed based on biological growth physiology in which environmental conditions are provided for microorganisms to convert organics in wastewater to biomass growth, embodiments of the present invention provide a process that is based on a storage-oriented perspective. Generally, environmental conditions govern the fate and conversion of organic matter by microbial consortia as either storage (i.e., PHA or glycogen accumulation) or growth response (i.e., biomass assimilation). Embodiments of the present invention focus on recovering the organic carbon by storage as the intracellular biopolymer, PHA. This is provided by selecting a waste stream with particular constituent characteristics and employing operational criteria that foster PHA storage-oriented AS (instead of growth-oriented AS as in traditional wastewater treatment). Subsequently, the excess AS that is commonly wasted in a traditional WWTP can be collected and treated for the downstream beneficial use as the AS contains a substantially higher amount of PHA.

In accordance with embodiments of the present invention, a waste stream that is suitable for enhanced PHA production is initially selected. In particular, this may include evaluating the constituents of existing waste streams to identify a rapidly biodegradable, high carbon-content waste stream having PHA precursor metabolites such that the waste stream promotes a rapid mass transport of the substrate within microbial cells, which subsequently triggers the microbial storage-response metabolism. The constituents of a waste steam evaluated may include the short chain fatty acids (SCFAs) concentration, the polysaccharides concentration, and the protein concentration.

SCFAs, which are fatty acids with aliphatic tails of six or fewer carbons, are primary precursor metabolites for PHA production. Accordingly, the waste stream should have a minimum level of SCFAs to promote PHA production. In some embodiments, a waste stream with a SCFAs concentration greater than 1 mM is preferred.

Polysaccharides and protein each provide competition with (and therefore interfere with) the production of PHA. In particular, given that polysaccharides and protein are two main cell components, a relatively high polysaccharide and protein content favors assimilation into microbial biomass and, therefore, fewer PHA storage polymers. The environmental conditions provided in the main reactor enrich microbial storage capacity. However, high polysaccharide content waste streams may result in the storage of glycogen (i.e., a type of polysaccharides) instead of PHAs. In some embodiments of the present invention, a waste stream having a polysaccharides concentration less than 6 mM and a protein concentration less than 1 mM is preferred.

The waste stream may further be evaluated for compounds toxic to bacteria. Preferably, the waste stream includes little to no toxic compounds to provide a non-toxic environment for microbes to survive and generate PHA.

In some embodiments, a waste stream may be selected with constituents that do not have a satisfactory SCFAs concentration, polysaccharides concentration, and/or protein concentration. In such embodiments, a pre-treatment process, such as fermentation of solids, may be employed to provide a pre-treated waste stream that meets the constituent criteria discussed above.

Solids may also interfere with reactor operation and "dilute" PHA content in the end products (i.e., PHA-laden biomass) while harvesting. Accordingly, in some embodiments, a waste stream is selected with minimum solids interference. Preferably, the waste stream has a total suspended solids (TSS) concentration less than 200 mg/L. If a waste stream is selected that has an undesirable level of solids (e.g., a TSS concentration more than 200 mg/L), a pre-treatment process, such as clarification or filtration, may be employed to produce a pre-treated waste stream with reduced solids to minimize solids interference with PHA production.

With reference now to FIG. 1, a schematic view is provided that illustrates a wastewater treatment process 100 that provides concurrent PHA production in accordance with an embodiment of the present invention. As shown in FIG. 1, an influent waste stream 102 is treated in a manner to encourage PHA production during the treatment process. In some embodiments, the influent waste stream 102 is an untreated waste stream that includes the constituent characteristics (e.g., satisfactory SCFAs concentration, polysaccharides concentration, protein concentration, and suspended solids concentration) as described hereinabove. However, in other embodiments, one or more pre-treatment processes 104 may optionally be provided to produce the influent waste stream 102. The pre-treatment processes may include fermentation or other process to provide a satisfactory SCFAs concentration, polysaccharides concentration, and/or protein concentration. Additionally or alternatively, the pre-treatment processes 104 may include a solids removal process, such as clarification or filtration, to reduce the suspended solids concentration of the influent waste stream 102.

The influent waste stream 102 is introduced into an aeration basin 106 and mixed with return activated sludge (RAS) 108. In some embodiments, the aeration basin 106 may be operated as a plug-flow reactor. Additionally, the aeration basin 106 is configured with operational parameters that provide sufficient reaction time and a food to microorganism (F/M) ratio for microorganisms to uptake and deplete the substrate. The configuration ensures a famine-feast regime to select and enrich microbes capable of producing PHA. Under a feast-famine dynamic feeding pattern, AS is subjected to successive periods of external substrate availability (i.e., feast stage) and unavailability (i.e., famine stage), which generates a selective pressure that ensures microorganisms capable of generating internal storage reserves have a strong competitive advantage over those without the storage capacity. In particular, during the feast stage, microorganisms uptake available external substrate and convert it into intracellular PHA. Subsequently, PHA accumulating microorganisms consume PHA as an internal carbon source for survival during famine stage (i.e., external substrate unavailability). With respect to substrate availability, a conventional growth-oriented wastewater treatment process provides a feast stage until the external substrate is depleted; after which, treated effluent is ready to discharge. As such, in accordance with embodiments of the present invention, the location at which the influent waste stream 102 is introduced (as described in further detail below) coupled with the operational parameters of the aeration basin 106 provide a famine-feast regime (i.e., an additional famine region in front of the feast region).

The operational parameters used to provide the famine-feast regime to promote PHA production in some particular embodiments may include influent COD (chemical oxygen demand) loading rate, hydraulic retention time (HRT), and F/M ratio. Generally, the influent COD loading rate may be higher than a conventional AS process. In some embodiments, the influent COD loading rate is between 800 mg/L/day and 3,500 mg/L/day. The F/M ratio is a commonly used process parameter used to describe operating conditions and is measured as a ratio of COD mg/L to MLVSS (mixed liquor volatile suspended solids) mg/L. The F/M ratio may be higher than a conventional AS process; preferably, the F/M ratio is between 0.8 and 3.

The HRT may be higher than a conventional AS process. In some embodiments, longer HRTs, such as 2 or more days, may be employed to further promote the famine-feast regime. However, in other embodiments, the HRT may be as low as 1.5 days. To achieve a lower HRT (i.e., 1.5 days), the process reactor can initially be operated at a higher HRT (e.g., 2 or more days) to provide an environment that optimizes selecting/enriching microorganism capable of producing PHA. Those microorganisms may then be used to seed a process reactor with lower HRTs (e.g., 1.5 days).

As shown in FIG. 1, the RAS 108 is introduced substantially at the beginning of the aeration basin 106, while the influent waste stream 102 is introduced further down the aeration basin 106. In some embodiments, the influent waste stream 102 is introduced at a location that ranges from approximately ¼ to ¾ along the length of the aeration basin 106. Introducing the RAS 108 at the beginning of the aeration basin 106 while introducing the influent waste stream 102 further down the aeration basin 106 in this manner promotes the famine-feast regime that provides an environment that favors microorganisms capable of accumulating PHA. Therefore, an additional famine region in front of feast region promotes the enrichment/selection of PHA accumulating microorganisms. Additionally, maximum PHA production occurs at the end of the aeration basin 106/wastewater treatment (i.e. end of feast stage) as it is ready to be collected for downstream beneficial use. Meanwhile, the treated effluent is ready to discharge (since the external substrate is depleted at the end of the feast stage).

A treated waste stream 110 exiting the aeration basin 106 is processed in a solids separation basin 112, such as a clarifier, to separate AS 114 from an effluent 116. A first portion of the AS 108 is returned to the aeration basin 106 as the RAS 108. A second portion of the AS 118 is provided as a PHA-laden biomass to a separation and stabilization process 120. The separation and stabilization process 120 prevents microbes from consuming PHA as an internal carbon source following harvest and thereby produces a stabilized PHA-laden biomass 122. In some embodiments, the separation and stabilization process 120 may include dewatering (e.g., centrifugation) followed by microbial inactivation (e.g., disinfection) and an ensuing drying process.

Although only a single aeration basin 106, solids separation basin 112, and separation and stabilization process 120 are shown in FIG. 1, it should be understood that multiple aeration basins, solid separation basins, and separation and stabilization processes may be operated in parallel in accordance with embodiments of the present invention. Additionally, further basins and processes (such as a SBR) not shown in FIG. 1 may be employed. Any and all such variations are contemplated to be within the scope of embodiments of the present invention.

Figure 2:
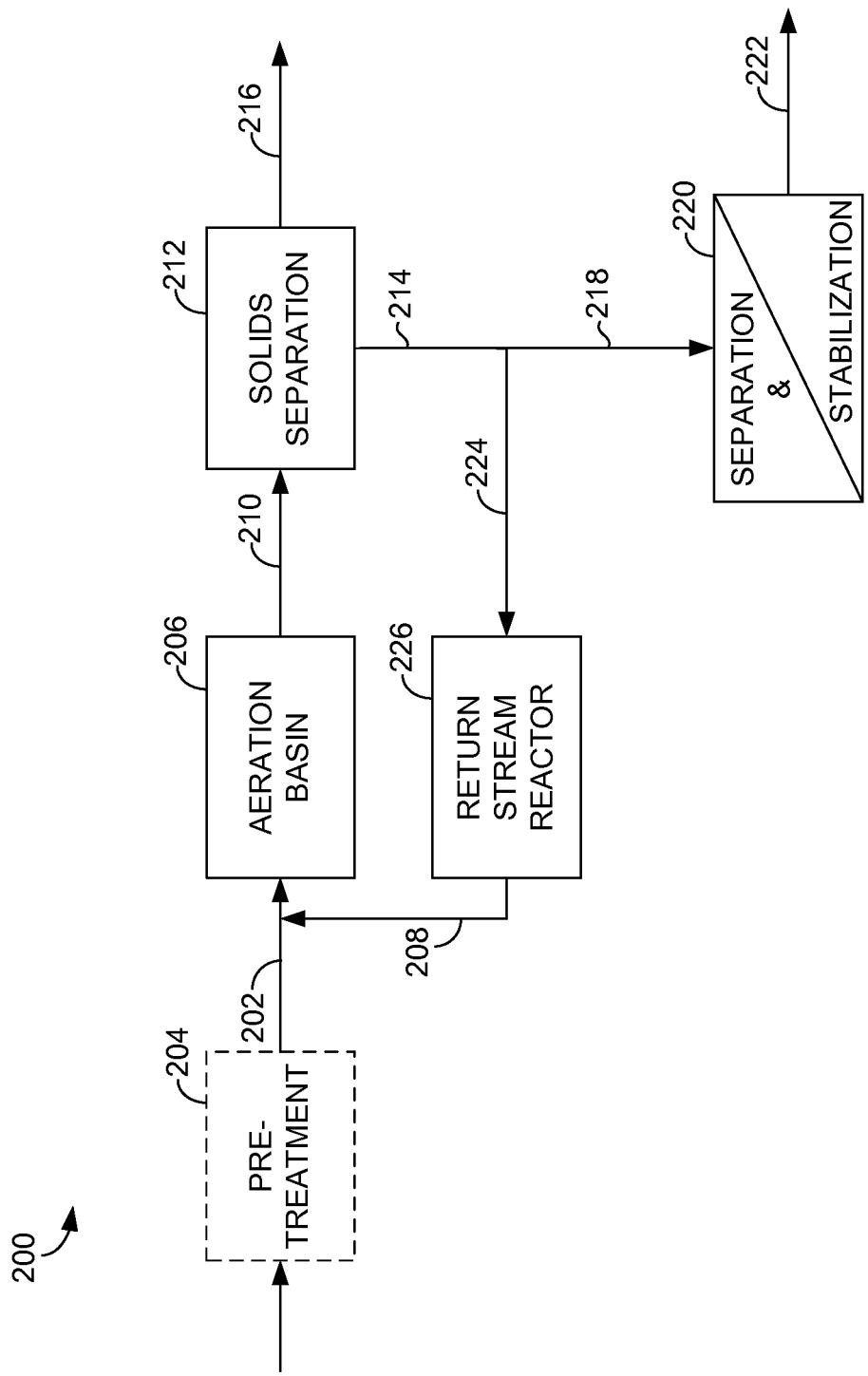
FIG. 2 illustrates a schematic diagram of PHA production during waste stream reclamation/organic resource recovery using a return stream reactor in accordance with another embodiment of the present invention.

While FIG. 1 illustrates an embodiment employing a single reactor (i.e., aeration basin 106), further embodiments may employ a return stream reactor in addition to a main stream reactor to provide the famine stage and feast stage separately that promotes PHA production. Turning now to FIG. 2, a schematic diagram is provided showing an embodiment of a process 200 employing a return stream reactor 226 in addition to an existing aeration basin 206. In some embodiments, an existing wastewater treatment process may be identified with an existing aeration basin (e.g., aeration basin 206), and the wastewater treatment process may be modified by adding a return stream reactor (e.g., return stream reactor 226) to provide a process (i.e., famine stage) that optimizes PHA production.

In accordance with the embodiment shown in FIG. 2, an influent waste stream 202 is provided that has constituent characteristics as described hereinabove. In some embodiments, this may optionally include a pre-treatment process 204, such as fermentation of solids and/or solids separation. The influent waste stream 202 and a RAS 208 are introduced into an aeration basin 206. In some embodiments, the operational parameters of the aeration basin 206 may include an HRT may be slightly higher than or equal to a conventional AS process, whereas the F/M ratio may be higher than or equal to a conventional AS process. In some particular embodiments, the operational parameters may include an HRT of approximately 8 hours to 2 days and an F/M ratio of 0.5 to 2.

A treated waste stream 210 from the aeration basin 206 is processed in a solids separation basin 212, such as a clarifier, to separate AS 214 from an effluent waste stream 216. A first portion of the AS 224 is introduced into a return stream reactor 226. In some embodiments, the return stream reactor 226 may be operated under an HRT of approximately 1 to 3 days and an F/M ratio of approximately 0.1 to 0.4.

A second portion of the activate sludge 218 is provided as a PHA-laden biomass to a separation and stabilization process 220. Similar to that discussed above with reference to FIG. 1, the separation and stabilization process 220 prevents microbes from consuming PHA as an internal carbon source following harvest and thereby produces a stabilized PHA-laden biomass 222. In some embodiments, the separation and stabilization process 220 may include dewatering (e.g., centrifugation) following by microbial stabilization (e.g., disinfection) and an ensuing drying process.

EXAMPLE

Embodiments of the present invention will now be further illustrated by the following, non-limiting examples.

Example 1

An industrial waste stream (e.g., high-strength COD) was found to be with COD of 2,500 mg/L, SCFAs of 1.2 mM, polysaccharides of 0.8 mM, protein of 0.4 mM, and TSS of 500 mg/L. As this waste stream met the constituents criteria with the exception of TSS, solid separation was employed as a pre-treatment process to reduce solids to a desirable level of TSS less than 200 mg/L in a pre-treated waste stream. The pre-treated waste stream was then introduced at a location approximately one-third along the length of an aeration basin. The aeration basin was operated under a HRT of 3 days and F/M ratio of 1.5. RAS was introduced at the beginning of the aeration basin. In this manner, the aeration basin provided a famine-feast regime that enriched/selected microorganisms capable of accumulating PHA. A treated waste stream exiting the aeration basin was processed in a clarifier to separate AS from an effluent. A first portion of the AS was returned to the aeration basin (as noted above). A second portion of the AS was treated using centrifugation followed by disinfection and an ensuing drying process to provide a stabilized PHA-laden biomass. Meanwhile, the effluent was ready to discharge.

Example 2

As a prophetic example of an embodiment employing a return stream reactor in addition to an aeration basin, a municipal wastewater treatment plant wastewater (e.g., low-strength COD waste stream) with COD of 250 mg/L, SCFAs of 0.2 mM, polysaccharides of 0.3 mM, protein of 0.2 mM, and TSS of 80 mg/L after existing primary sedimentation is processed. As this waste stream is not in a preferred range of COD and SCFAs concentration, a fermentation pre-treatment process is employed as a pre-treatment (e.g., primary solids fermentation) to increase COD and SCFAs to a desirable level of COD loading more than 800 mg/L/d and SCFAs concentration more than 1 mM to provide constituent characteristics. In addition, solids collected from the primary sedimentation are introduced into the fermentor to increase COD and SCFAs concentration in the influent waste stream. The influent waste stream and a RAS are introduced into an aeration basin. The aeration basin is operated under HRT of approximately 1 day and F/M ratio of 0.8. A treated waste stream from the aeration basin is processed in a clarifier to separate AS from an effluent. A first portion of the AS is introduced into a return stream reactor. The return stream reactor is operated under HRT of 2.5 days and the F/M ratio of approximately 0.2. A second portion of the AS is separated by centrifugation followed by disinfection and an ensuing drying process to provide a stabilized PHA-laden biomass. Meanwhile, the effluent is ready to discharge.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated by and is within the scope of the claims.

What is claimed is:

1. A process for polyhydroxyalkanoate (PHA) production during wastewater treatment, the process comprising:
   introducing a return activated sludge (RAS) into an aeration basin at a first location;
   introducing a waste stream suitable for increased PHA production into the aeration basin at a second location along the length of the aeration basin that is a distance downstream from the first location to provide a first zone upstream from the second location at which the waste stream is introduced followed by a second zone downstream from the second location at which the waste stream is introduced, the first zone selecting microorganisms capable of accumulating PHA, the second zone promoting the production of PHA by the microorganisms in the aeration basin;
   operating the aeration basin under operational parameters in which the first zone selects microorganisms capable of accumulating PHA followed by the second zone that promotes the production of PHA by the microorganisms in the aeration basin;

processing a treated waste stream from the aeration basin to separate activated sludge (AS) from an effluent, wherein a first portion of the AS is returned to the aeration basin as the RAS; and processing a second portion of the AS to produce a stabilized PHA-laden biomass.

2. The process of claim 1, wherein the process further comprises:

evaluating characteristics of the waste stream; and determining that the waste stream is suitable for increased PHA production based on the characteristics of the waste stream.

3. The process of claim 2, where the characteristics of the waste stream evaluated comprise a short chain fatty acids concentration, a polysaccharides concentration, a protein concentration, and a total suspended solids concentration.

4. The process of claim 1, wherein the process further comprises pre-treating an initial waste stream to produce the waste stream suitable for increased PHA production.

5. The process of claim 4, wherein pre-treating the initial waste stream comprises processing the initial waste stream using solids fermentation.

6. The process of claim 4, wherein pre-treating the initial waste stream comprises reducing total suspended solids.

7. The process of claim 1, wherein the location at which the waste stream is introduced into the aeration basin ranges from ¼ to ¾ along the length of the aeration basin.

8. The process of claim 1, wherein the waste stream has short chain fatty acids more than 1 mM.

9. The process of claim 1, wherein the waste stream has polysaccharides less than 6 mM.

10. The process of claim 1, wherein the waste stream has protein less than 1 mM.

11. The process of claim 1, wherein the waste stream has total suspended solids concentration less than 200 mg/L.

12. The process of claim 1, wherein the aeration basin is operated as a plug-flow reactor.

13. The process of claim 1, wherein the operational parameters for the aeration basin include an influent chemical oxygen demand (COD) loading rate between 800 mg/L/day and 3,500 mg/L/day.

14. The process of claim 1, wherein the operational parameters for the aeration basin include a hydraulic retention time more than 1.5 days.

15. The process of claim 1, wherein the operational parameters for the aeration basin include a food-to-microorganism ratio between 0.8 and 3.

16. The process of claim 1, wherein processing the second portion of the AS to produce the stabilized PHA-laden biomass comprises processing the second portion of the AS using dewatering, microbial inactivation, and drying.

17. A process for polyhydroxyalkanoate (PHA) production during wastewater treatment, the process comprising:

providing a waste stream suitable for increased PHA production;

introducing the waste stream and a return activated sludge (RAS) into an aeration basin;

operating the aeration basin as a conventional activated sludge (AS) process under operational parameters that promote the production of PHA;

processing a treated waste stream from the aeration basin to separate AS from an effluent;

introducing a first portion of the AS into a return stream reactor, wherein an effluent AS from the return stream reactor is returned to the aeration basin as the RAS;

operating the return stream reactor under operational parameters that select microorganisms capable of producing PHA, the operational parameters for the return stream reactor including a hydraulic retention time between 1 day and 3 days; and processing a second portion of the AS to produce a stabilized PHA-laden biomass.

18. The process of claim 17, wherein the operational parameters for the return stream reactor include a food-to-microorganism ratio between 0.1 and 0.4.

19. A process for polyhydroxyalkanoate (PHA) production during wastewater treatment, the process comprising:

introducing a return activated sludge (RAS) into an aeration basin operating as a plug-flow reactor at a first location;

identifying a biodegradable, high-carbon content waste stream having PHA precursor metabolites, the waste stream having a short chain fatty acids more than 1 mM, polysaccharides less than 6 mM, protein less than 1 mM, and total suspended solids concentration less than 200 mg/L;

introducing the waste stream into the aeration basin at a second location ¼ to ¾ along the length of the aeration basin downstream from the beginning of the aeration basin and the first location to provide a first zone upstream from the second location at which the waste stream is introduced followed by a second zone downstream from the second location at which the waste stream is introduced, the first zone selecting microorganisms capable of accumulating PHA, the second zone promoting the production of PHA by the microorganisms in the aeration basin;

operating the aeration basin with the following operational parameters: an influent chemical oxygen demand (COD) loading rate between 800 mg/L/day and 3,500 mg/L/day, a hydraulic retention time more than 1.5 days, and a food-to-microorganism ratio between 0.8 and 3 to provide a regime in which the first zone selects microorganisms capable of accumulating PHA followed by the second zone that promotes the production of PHA by the microorganisms;

transferring a treated waste stream from the aeration basin to a clarifier that separates activated sludge (AS) from an effluent, wherein a first portion of the AS is returned to the aeration basin as the RAS; and separating and stabilizing PHA-laden biomass from a second portion of the AS.

* * * * *